United States Patent
Faler et al.

(10) Patent No.: US 10,815,255 B2
(45) Date of Patent: Oct. 27, 2020

(54) SYNTHESIS OF BENZYLOXYPHENOXY PHENOL LIGANDS

(71) Applicant: Univation Technologies, LLC, Houston, TX (US)

(72) Inventors: Catherine A. Faler, Houston, TX (US); C. Jeff Harlan, Houston, TX (US)

(73) Assignee: Univation Technologies, LLC, Houston, TX (US)

( * ) Notice: Subject to any disclaimer, the term of this patent is extended or adjusted under 35 U.S.C. 154(b) by 0 days.

(21) Appl. No.: 16/475,819

(22) PCT Filed: Jan. 5, 2018

(86) PCT No.: PCT/US2018/012461
§ 371 (c)(1),
(2) Date: Jul. 3, 2019

(87) PCT Pub. No.: WO2018/129235
PCT Pub. Date: Jul. 12, 2018

(65) Prior Publication Data
US 2019/0352314 A1 Nov. 21, 2019

Related U.S. Application Data

(60) Provisional application No. 62/443,450, filed on Jan. 6, 2017.

(51) Int. Cl.
*C07F 7/00* (2006.01)
*C07C 41/14* (2006.01)
*C07C 43/178* (2006.01)
*C07C 43/225* (2006.01)
*C07C 43/23* (2006.01)

(52) U.S. Cl.
CPC .............. *C07F 7/003* (2013.01); *C07C 41/14* (2013.01); *C07C 43/1786* (2013.01); *C07C 43/225* (2013.01); *C07C 43/23* (2013.01)

(58) Field of Classification Search
None
See application file for complete search history.

(56) References Cited

U.S. PATENT DOCUMENTS

2004/0005984 A1   1/2004   Boussie et al.

FOREIGN PATENT DOCUMENTS

WO   2016172110   10/2016
WO   2016172114   10/2016

OTHER PUBLICATIONS

International Preliminary Report on Patentability for related PCT Application PCT/US2018/012461, dated Jul. 18, 2019 (8 pgs).
International Search Report & Written Opinion for related PCT Application PCT/US2018/012461, dated Mar. 28, 2018 (12 pgs).

*Primary Examiner* — Clinton A Brooks
(74) *Attorney, Agent, or Firm* — Brooks, Cameron & Huebsch, PLLC

(57) ABSTRACT

Synthetic methods for the preparation of ligands and metal-ligand complexes are disclosed.

6 Claims, No Drawings

SYNTHESIS OF BENZYLOXYPHENOXY PHENOL LIGANDS

This application is a National Stage Application under 35 U.S.C. § 371 of International Application Number PCT/US2018/012461, filed Jan. 5, 2018 and published as WO 2018/129235 on Jul. 12, 2018, which claims the benefit to U.S. Provisional Application 62/443,450, filed Jan. 6, 2017, the entire contents of which are incorporated herein by reference in its entirety.

The invention relates to ligands, complexes, and/or catalysts that provide olefin polymerization capabilities.

BACKGROUND OF THE INVENTION

Ligand-metal coordination complexes, e.g., organometallic complexes, are useful as catalysts, additives, stoichiometric reagents, monomers, solid-state precursors, therapeutic reagents and drugs. Complexes of this type ordinarily are prepared by combining a ligand with a suitable metal compound or metal precursor in a suitable solvent at a suitable temperature. The ligand contains functional groups that bind to the metal center(s), remain associated with the metal center(s), and therefore provide an opportunity to modify the steric, electronic and chemical properties of the active metal center(s) of the complex.

Certain ligand-metal complexes are catalysts for reactions such as oxidation, reduction, hydrogenation, hydrosilylation, hydrocyanation, hydroformylation, polymerization, carbonylation, isomerization, metathesis, carbon-hydrogen activation, carbon-halogen activation, cross-coupling, Friedel-Crafts acylation and alkylation, hydration, dimerization, trimerization, oligomerization, Diels-Alder reactions and other transformations. In the field of polymerization catalysis, in connection with single site catalysis, the ligand typically offers opportunities to modify the electronic and/or steric environment surrounding an active metal center. This allows the ligand to assist in the creation of possibly different polymers. Group 4 metallocene based single site catalysts are generally known for polymerization reactions.

One application for metallocene catalysts is producing isotactic polypropylene. Isotactic polypropylene and its production has been extensively studied. See, e.g., US 2004/0005984 A1.

In view of the industrial importance of this field, it would be desirable to have additional synthetic methods for the preparation of ligands.

SUMMARY OF THE INVENTION

The invention includes a process for preparing a ligand, the process comprising contacting a first reactant with a bridging reactant in a polar aprotic reaction medium under reaction conditions, thereby forming the ligand; wherein: (a) when the first reactant is 2-((tetrahydro-2H-pyran-2-yl)oxy)-[1,1'-biphenyl]-3-yl lithium, the bridging reactant is 2-bromo-1-(3-((2-bromobenzyl)oxy)propoxy)-4-methylbenzene, and the ligand is 2-(3-((2'-hydroxy-[1,1':3',1''-terphenyl]-2-yl)methoxy)propoxy)-5-methyl-[1,1':3',1''-terphenyl]-2'-ol (Ligand AP); or wherein (b) when the first reactant is 2',5,5'-trimethyl-2-((methoxymethoxy)-[1,1'-biphenyl]-3-yl lithium, the bridging reactant is 2-bromo-1-(3-((2-bromobenzyl)oxy)propoxy)-4-methylbenzene, and the ligand is 2-(3-((2'-hydroxy-2'',5',5''-trimethyl-[1,1':3',1''-terphenyl]-2-yl)methoxy)propoxy)-2'',5,5',5''-tetramethyl-[1,1':3',1''-terphenyl]-2'-ol (Ligand BP); or wherein (c) when the first reactant is 2-(methoxymethoxy)-5-methyl-3-(2-methylnaphthalen-1-yl)phenyl) lithium, the bridging reactant is 2-bromo-1-(3-((2-bromobenzyl)oxy)propoxy)-4-methylbenzene, and the ligand is 2'-(3-((2'-hydroxy-5'-methyl-3'-(2-methylnaphthalen-1-yl)-[1,1'-biphenyl]-2-yl)methoxy)propoxy)-5,5'-dimethyl-3-(2-methylnaphthalen-1-yl)-[1,1'-biphenyl]-2-ol (Ligand CP). The invention also includes a process for preparing analogous Ligands AE, BE, and CE.

The ligands of the process of the invention are useful in the preparation of catalysts for the polymerization of olefins.

DETAILED DESCRIPTION OF THE INVENTION

As used herein, the terms "a," "an," "the," "at least one," and "one or more" are used interchangeably. The terms "comprises" and "includes" and variations thereof do not have a limiting meaning where these terms appear in the description and claims. Thus, for example, a composition that includes "a" material can be interpreted to mean that the composition includes "one or more" materials.

"Complex" means a coordination compound formed by the union of one or more electronically rich molecules or atoms capable of independent existence with one or more electronically poor molecules or atoms, each of which is also capable of independent existence.

All references to the "Periodic Table of Elements" and the various groups within the Table are to the Table as published in the *CRC Handbook of Chemistry and Physics*, 71$^{st}$ Ed. (1990-1991), CRC Press, at page 1-10.

The term "reaction medium" includes, but is not limited to, a liquid in which at least one reactant is at least partially soluble. Thus, for a given reaction, it is possible that all reactants are solubilized in the reaction medium, but it is also possible that the reactants form a suspension in the reaction medium. Other combinations are also possible. As used herein, the term "solvent" is interchangeable with the term reaction medium.

Unless stated to the contrary, implicit from the context, or customary in the art, all parts and percentages are based on weight and all test methods are current as of the filing date of this disclosure.

As used herein, "Bn" refers to benzyl, and DIAD refers to diisopropyl azodicarboxylate.

The invention includes processes for the preparation of ligands and ligand-metal complexes. For example, one process of the invention comprises the following steps:

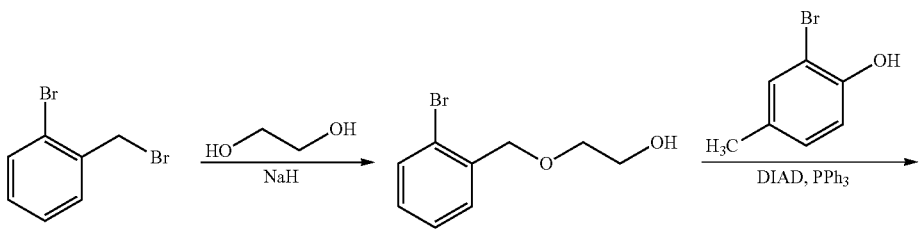

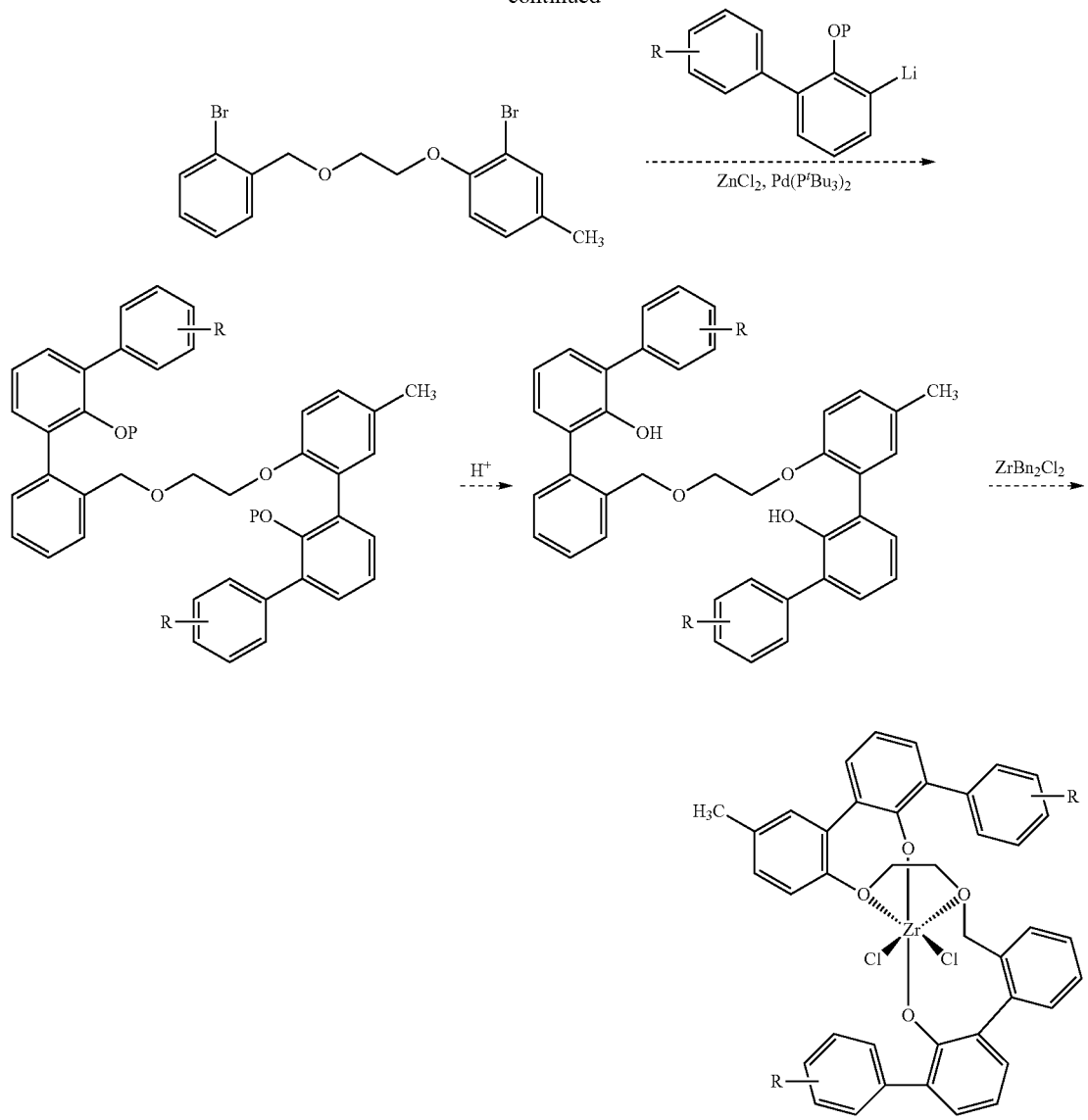

(Ligand AE, when R = H))

wherein R can be H or lower alkyl, preferably H or methyl, Bn is benzyl, Bu is butyl, $^t$Bu is tert-butyl, and Ph represents phenyl. Zr in the preceding structure can be more generally replaced by M, representing a metal, which is described in more detail below.

The term "alkyl" as used herein refers to a branched or unbranched saturated hydrocarbon group typically although not necessarily containing 1 to about 50 carbon atoms. The term "lower alkyl" refers to alkyl groups of 1 to 6, preferably 1 to 4, carbon atoms. Examples of lower alkyl groups include methyl, ethyl, n-propyl, isopropyl, n-butyl, t-butyl and iso-butyl.

This reaction scheme may also be conducted starting with diols other than ethylene glycol, e.g. 1,3-propanediol. For example, the following reaction scheme can be employed.

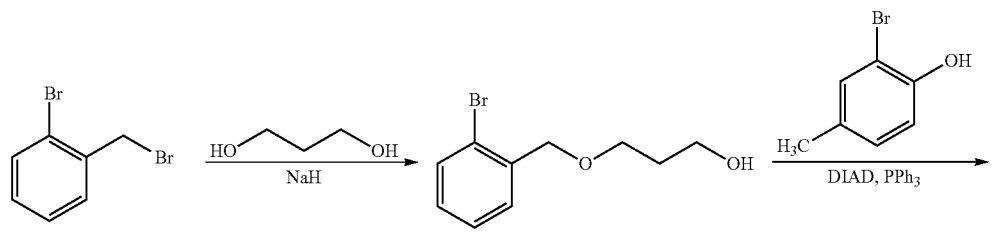

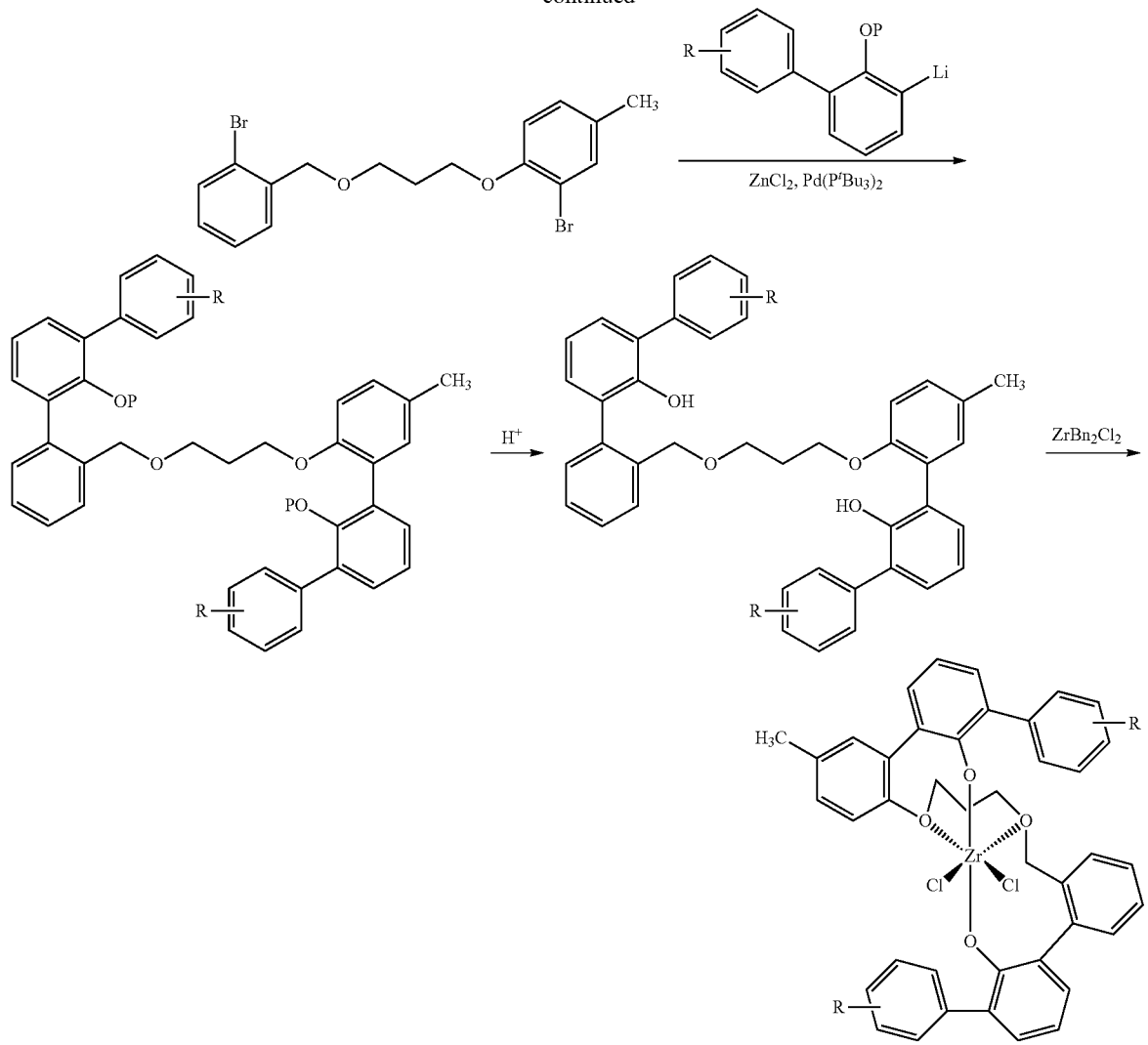

(Ligand AP, when R = H))

wherein R can be H or lower alkyl, preferably H or methyl, Bn is benzyl, Bu is butyl, $^tBu$ is tert-butyl, and Ph represents phenyl. Zr in the preceding structure can be more generally replaced by M, representing a metal, which is described in more detail below.

Other variations on the scheme are described hereinbelow. In one embodiment of the invention, reactions are conducted under an inert gas atmosphere such as an anhydrous gas of $N_2$, Ar, He, or mixtures thereof. In one embodiment of the invention, the reactions are conducted at around ambient pressure.

The process description that follows for the first step of the reaction is one way of performing the reactions of the invention, but one skilled in the art would readily know how to use other reaction conditions (e.g., different temperatures), solvents (e.g., different solvents), and reagents (e.g., LiH instead of NaH) in alternative embodiments to carry out the reactions.

For example, in one embodiment of the invention, sodium hydride is reacted with 1,3-propanediol in a reaction medium to form an intermediate compound, which is then reacted with 2-bromobenzylbromide to form 3-((2-bromobenzyl)oxy)propan-1-ol. The reaction may be conducted at a temperature of from −75 to 75° C., preferably from −50 to 50° C. In one embodiment of the invention, in the first step of the reaction scheme shown above, sodium hydride is suspended in a polar aprotic reaction medium, such as tetrahydrofuran (THF) and the mixture is cooled to a temperature of from −75 to 25° C. 1,3-propandiol then is added slowly (Caution: $H_2$ generated) and the resulting mixture is allowed to warm to from 1 to 70° C., more preferably ambient temperature. 2-bromobenzylbromide is then added with stirring and the reaction is allowed to go to completion to form the product, 3-((2-bromobenzyl)oxy)propan-1-ol.

The process description that follows for the second step of the reaction is one way of performing the reactions of the invention, but one skilled in the art would readily know how to use other reaction conditions (e.g., different temperatures), solvents (e.g., different solvents), and reagents in alternative embodiments to carry out the reactions. For example, in one embodiment of the invention, 3-((2-bromobenzyl)oxy)propan-1-ol is contacted in a reaction medium with bromocresol, triphenylphosphine and DIAD to form 2-bromo-1-(3-((2-bromobenzyl)oxy)propoxy)-4- methylbenzene. The reaction may be conducted at a temperature of from 0 to 70° C., preferably from 10 to 50° C. In one embodiment of the invention, in the second step of the reaction scheme shown above, 3-((2-bromobenzyl)oxy)propan-1-ol, bromocresol, and triphenylphosphine are dissolved in a polar aprotic reaction medium, such as THF, and then DIAD is added slowly as the colorless solution slowly turns yellow. The reaction is allowed to stir at a temperature of from 0 to 70° C., more preferably ambient temperature, to allow the reaction to form the product 2-bromo-1-(3-((2-bromobenzyl)oxy)propoxy)-4-methylbenzene.

The process description that follows for the third step of the reaction is one way of performing the reactions of the invention, but one skilled in the art would readily know how to use other reaction conditions (e.g., different temperatures), solvents (e.g., different solvents), and reagents in alternative embodiments to carry out the reactions. For example, in one embodiment of the invention, 2-((tetrahydro-2H-pyran-2-yl)oxy)-[1,1'-biphenyl]-3-yl lithium is contacted in a reaction medium with a metal chloride, 2-bromo-1-(3-((2-bromobenzyl)oxy)propoxy)-4-methylbenzene and a metal phosphine. to form the desired product. The reaction may be conducted at a temperature of from 0 to 125° C., preferably from 20 to 95° C. In one embodiment of the invention, in the third step of the reaction scheme shown above, R=H. 2-((tetrahydro-2H-pyran-2-yl)oxy)-[1,1'-biphenyl]-3-yl lithium is slurried in a polar aprotic reaction medium, preferably THF, then a metal chloride, preferably zinc chloride, is added to the mixture and the mixture is stirred, followed by the addition of 2-bromo-1-(3-((2-bromobenzyl)oxy)propoxy)-4-methylbenzene, followed by the addition of a metal phosphine, preferably palladium bis(tri-tert-butylphosphine). The resulting brown solution is heated to a temperature of from 50 to 95° C., and the reaction is then quenched and extracted with an organic solvent. The solvent is removed, preferably under reduced pressure, and the remaining oil is redissolved in a solvent mixture, preferably THF/methanol. The mixture is acidified, e.g. with HCl, and the solution is stirred to allow the product ligand, 2-(3-((2'-hydroxy-[1,1':3',1''-terphenyl]-2-yl)methoxy)propoxy)-5-methyl-[1,1':3',1''-terphenyl]-2'-ol, to form.

A ligand metal complex may be formed in a subsequent step if desired. The process description that follows for the complex-forming step is one way of performing it, but one skilled in the art would readily know how to use other reaction conditions (e.g., different temperatures), solvents (e.g., different solvents), and reagents in alternative embodiments to carry out the reaction. For example, in one embodiment of the invention, the ligand 2-(3-((2'-hydroxy-[1,1':3',1''-terphenyl]-2-yl)methoxy)propoxy)-5-methyl-[1,1':3',1''-terphenyl]-2'-ol is dissolved in a solvent and is contacted with a metal precursor ML to form the ligand metal complex. In one embodiment of the invention, the ligand 2-(3-((2'-hydroxy-[1,1':3',1''-terphenyl]-2-yl)methoxy)propoxy)-5-methyl-[1,1':3',1''-terphenyl]-2'-ol is dissolved in a nonpolar solvent, e.g. toluene. Then, a toluene solution of bis-benzyl-zirconium(IV) dichloride (ZrBn$_2$Cl$_2$) is added to the ligand solution. The mixture is stirred then heated at an elevated temperature, e.g. 25 to 120° C., preferably from 75 to 95° C., and the zirconium complex shown above is formed.

The catalysts in some embodiments are compositions comprising the ligand and metal precursor, and optionally may additionally include an activator, combination of activators or activator package. In other embodiments, the catalysts are metal-ligand complexes and optionally may additionally include an activator, combination of activators or activator package.

For example, the metal-ligand complexes of this invention can be characterized by the general formula:

$$(4,2,O,S)ML_n. \qquad (I)$$

where (4,2,O,S) is a dianionic ligand having at least 4 atoms that are oxygen or sulfur and chelating to the metal M at least 2, preferably 4, coordination sites through oxygen and/or sulfur atoms; M is a metal selected from the group consisting of groups 3-6 and Lanthanide elements of the Periodic Table of Elements, preferably from group 4 (Hf, Zr and Ti); L is independently selected from the group consisting of halide (F, Cl, Br, I), and optionally two or more L groups may be linked together in a ring structure; and n is 1, 2, 3, or 4. In one embodiment of the invention, more than one ligand can complex to the same metal atom. This can be accomplished by adjusting the ratio of ligand to metal atoms in the complex forming step.

The ligands that are suitable for use in the catalysts herein have several general, alternative descriptions. In one embodiment, the ligands are dianionic, chelating ligands that may occupy up to four coordination sites of a metal atom. The ligands can also be described as dianionic ligands that, when chelated to a metal atom, form at least one or two metalocycles (counting the metal atom as one member of the ring). Also, in some embodiments, the ligands can be described as dianionic, chelating ligands that use either oxygen or sulfur as binding atoms to the metal atom. In still other embodiments, the ligands can be described as non-metallocene ligands that can coordinate in an approximate $C_2$-symmetrical complex with a metal atom. These embodiments can be used together or separately.

For example, suitable ligands useful in this invention may be characterized by the following formulas:

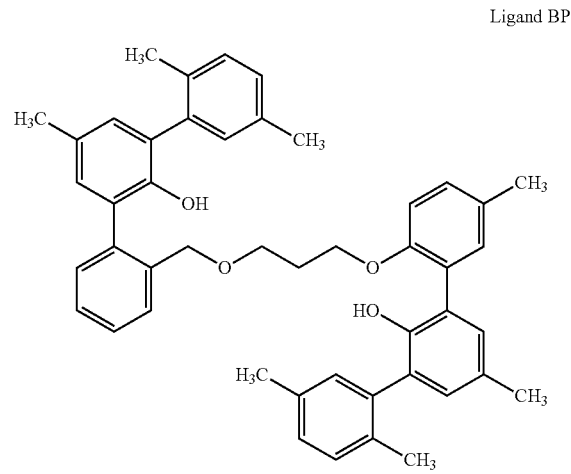

Ligand BP

-continued

Ligand CP

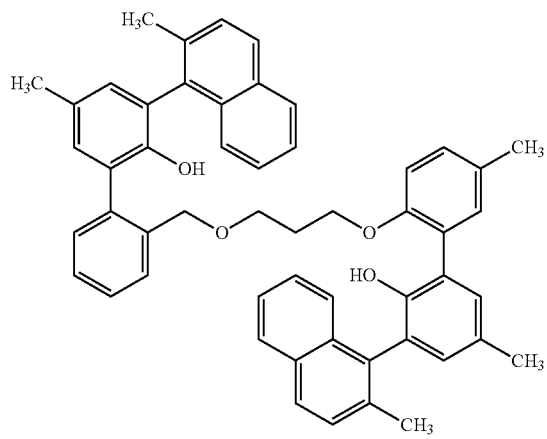

Note that Ligands BE and CE are analogous to Ligands BP and CP in that the ligands are identical except that Ligands BP and CP have a $C_3$ bridging moiety whereas Ligands BE and CE (not shown) have a $C_2$ bridging moiety. In the ligand "nickname" nomenclature used herein, the second letter denotes either a $C_2$ or $C_3$ bridging moiety; thus, the "E" in Ligand AE is intended to designate a Ligand A structure having a $C_2$ bridging moiety while, the "P" in Ligand AP is intended to designate a Ligand A structure having a $C_3$ bridging moiety. For example, compare the structures of Ligands AE and AP, both of which are included hereinabove.

The bridging moieties in the Ligands AP, BP and CP contain 3 carbon atoms, but the analogous Ligands AE, BE, and CE, containing 2 carbon atoms in the bridge, are also within the scope of the invention. For the purposes of this disclosure, any conflict between a structure and the name given to the structure is to be resolved in favor of the structure.

It is required that there be at least 2 hydrogen atoms associated with each ligand that are capable of being removed in a complexation reaction with a metal atom or metal precursor or base. In some embodiments, prior to such a complexation reaction, a base may be reacted with the ligand to form a salt, the product of which may then be reacted with a metal precursor ML, wherein M and L are as defined above.

In general, building blocks are prepared that are then linked together with a bridging group. Variations in the R group substituents can be introduced in the synthesis of the building blocks. Variations in the bridge can be introduced with the synthesis of the bridging group. The bridging reactant supplies the structure of the bridging moiety of a ligand. Similarly, the first reactant supplies all or part of the remainder of the ligand structure. Examples of bridging reactants and first reactants are given elsewhere herein.

Ligands within the scope of this invention may be prepared according to the general schemes shown above, where building blocks are first prepared and then coupled together with the proviso that similar schemes may be used to prepare ligands other than the ligands shown herein.

Once the desired ligand is formed, it may be combined with a metal atom, ion, compound or other metal precursor compound, e.g. ML, wherein M and L are as defined above. In some applications, the ligands of this invention will be combined with a metal compound or precursor and the product of such combination is not determined, if a product forms. For example, the ligand may be added to a reaction vessel at the same time as the metal or metal precursor compound along with the reactants, activators, scavengers, etc. Additionally, the ligand can be modified prior to addition to or after the addition of the metal precursor, e.g. through a deprotonation reaction or some other modification.

The ligand to metal precursor compound ratio advantageously is in the range of 0.01:1 to 100:1, more specifically in the range of 0.1:1 to 10:1 and even more specifically 1:1. Generally, the ligand is mixed with a suitable metal precursor and optionally other components, such as activators, prior to or simultaneously with allowing the mixture to be contacted with the reactants, e.g., monomers. When the ligand is mixed with the metal precursor compound, a metal-ligand complex may be formed, which may be a catalyst or may need to be activated to be a catalyst.

Activators and their use are well-known to those skilled in the art. Broadly speaking, the activator may comprise alumoxanes, Lewis acids, Bronsted acids, compatible non-interfering activators and combinations of the foregoing. These types of activators have been taught for use with different compositions or metal complexes in the following references, which are hereby incorporated by reference in their entirety: U.S. Pat. Nos. 5,599,761, 5,616,664, 5,453, 410, 5,153,157, and 5,064,802. In particular, ionic or ion forming activators are preferred.

The ligands, complexes or catalysts may be supported on organic or inorganic supports. Suitable supports include silicas, aluminas, clays, zeolites, magnesium chloride, and polymeric supports such as polystyrenes, substituted polystyrenes and the like. Polymeric supports may be cross-linked or not. In addition, the catalysts of this invention may be combined with other catalysts in a single reactor and/or employed in a series of reactors (parallel or serial) in order to form blends of polymer products.

The ligands, complexes and/or catalysts are particularly effective at polymerizing α-olefins (such as propylene, 1-butene, 1-pentene, 1-hexene, 1-heptene, 1-octene, and styrene), copolymerizing ethylene with α-olefins (such as propylene, 1-butene, 1-pentene, 1-hexene, 1-heptene, 1-octene, and styrene), and copolymerizing ethylene with 1,1-disubstituted olefins (such as isobutylene). These compositions might also polymerize monomers that have polar functionalities in homopolymerizations or copolymerizations and/or homopolymerize 1,1- and 1,2-disubstituted olefins. Also, diolefins in combination with ethylene and/or α-olefins or 1,1- and 1,2-disubstituted olefins may be copolymerized. Methods for polymerizing these monomers are well-known to those skilled in the art. The ligands, metal-ligand complexes and compositions of this invention can be prepared and tested for catalytic activity in one or more of the above reactions in a combinatorial fashion. Combinatorial chemistry generally involves the parallel or rapid serial synthesis and/or screening or characterization of compounds and compositions of matter. Methods of conducting combinatorial chemistry are well-known to those skilled in the art.

SPECIFIC EMBODIMENTS OF THE INVENTION

General:

All reagents are purchased from commercial vendors and used as received unless otherwise noted. Solvents are sparged with $N_2$ and dried over 3 Å molecular sieves. Analytical thin-layer chromatography (TLC) is performed on Selecto Plates (200 μm) precoated with a fluorescent indicator. Visualization is effected using ultraviolet light (254 nm). Flash column chromatography is carried out with Sigma Aldrich Silica gel 60 Å (70-230 mesh) using solvent systems specified. NMR spectra are recorded on a Bruker 400 and/or 500 NMR with chemical shifts referenced to residual solvent peaks.

Example 1—Preparation of 3-((2-bromobenzyl)oxy) propan-1-ol (509-18)

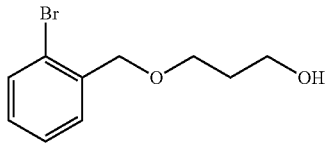 [SMILES: OCCCOCc1ccccc1Br]

Sodium hydride (95%, 1.0 g, 40 mmol) is suspended in 20 mL of THF and is cooled to −35° C. 1,3-propandiol (20 mL) is added slowly (Caution: $H_2$ generated) and the mixture is allowed to warm to ambient temperature over 10 min. 2-bromobenzylbromide (10 g, 40 mmol) is added and the reaction mixture is stirred for 4 h, and then is quenched with saturated ammonium chloride. The product is extracted with 3 portions of ethyl acetate, followed by washes with water and brine. The organic portion is dried over $MgSO_4$, is filtered and is concentrated to a clear colorless oil in 84% crude yield: Rf=0.33 (30:70 acetone:isohexane); $^1$H NMR (400 MHz, $CDCl_3$, δ): 1.91 (m, 2H), 2.46 (br s, 1H), 3.73 (m, 2H), 3.80 (m, 2H), 4.58 (s, 2H), 7.15 (m, 1H), 7.31 (m, 1H), 7.44 (d, J=7.5 Hz, 1H), 7.54 (m, 1H); $^{13}$C NMR (125 MHz, $CDCl_3$, δ): 32.4, 61.7, 69.8, 72.8, 123.1, 127.6, 129.2, 129.3, 132.8, 137.6; IR ($cm^{-1}$): 3381, 3064, 2945, 2868, 1568, 1440, 1100, 1026.

Example 2—Preparation of 2-bromo-1-(3-((2-bromobenzyl)oxy)propoxy)-4-methylbenzene (509-16)

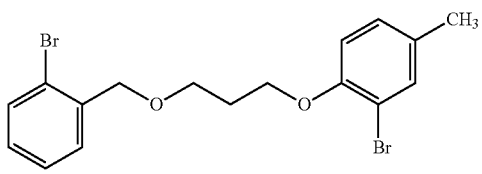 [SMILES: Cc1ccc(OCCCOCc2ccccc2Br)c(Br)c1]

The product of Ex. 1, namely alcohol 509-18, (6.0 g, 24.4 mmol), bromocresol (4.8 g, 25.6 mmol), and triphenylphosphine (6.7 g, 25.6 mmol) are dissolved in 50 mL of THF. DIAD (5.14 mL, 26.1 mmol) is added dropwise as the colorless solution slowly turns yellow. The reaction is allowed to stir at ambient temperature overnight then is quenched with saturated ammonium chloride. The mixture is extracted with ethyl acetate and is concentrated to a crude yellow oil. Pentane is slurried with the oil and the slurry is filtered through a plug of silica gel. The filtrate is concentrated giving the product as a yellow oil in 50% yield: Rf=0.50 (30:70 acetone:isohexane); $^1$H NMR (400 MHz, $CDCl_3$, δ): 2.16 (qn, J=6.0 Hz, 2H), 2.28 (s, 3H), 3.18 (t, J=6.0, 2H), 4.16 (t, J=6.0 Hz, 2H), 4.58 (s, 2H), 6.82 (d, J=8.5 Hz, 1H), 7.03 (m, 1H), 7.13 (m, 1H), 7.28 (m, 1H), 7.34 (s, 1H), 7.45 (m, 1H), 7.52 (m, 1H); $^{13}$C NMR (125 MHz, $CDCl_3$, δ): 20.4, 29.9, 66.3, 67.4, 72.7, 72.6, 112.2, 113.6, 123.0, 127.5, 129.0, 129.2, 129.3, 131.7, 132.7, 133.9, 137.9, 153.4.

Example 3—Preparation of 2-(3-((2'-hydroxy-[1,1': 3',1''-terphenyl]-2-yl)methoxy)propoxy)-5-methyl-[1,1':3',1''-terphenyl]-2'-ol (505-14) (Ligand AP)

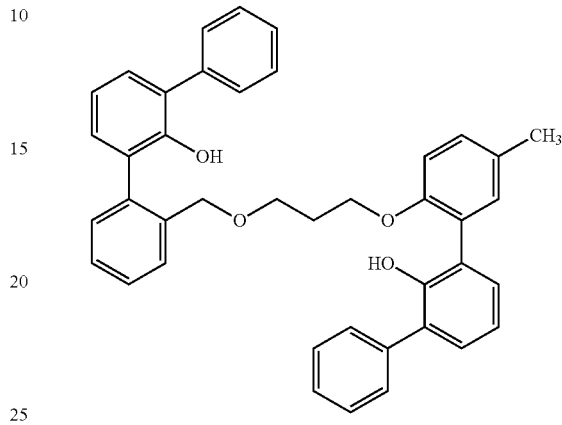

2-((tetrahydro-2H-pyran-2-yl)oxy)-[1,1'-biphenyl]-3-yl lithium (2.53 g, 7.57 mmol), a first reactant as that term is used herein, prepared from phenyl phenol, is slurried in 20 mL of THF. Zinc chloride (1.05 g, 15 mmol) is added and the reaction is stirred for approx. 3.5 min before the addition of the above dibromo compound 509-16 (1.62 g, 3.78 mmol) prepared in Ex. 2, which is a bridging reactant as that term is used herein, followed by palladium bis(tri-tert-butylphosphine) (120 mg, 0.23 mmol). The brown solution is heated at 75° C. for about 30 min. The reaction is quenched with water and is extracted with an organic solvent. The solvent is removed under reduced pressure and the remaining oil is redissolved in 40 mL of THF/methanol (3:5). Concentrated HCl (4 drops) is added, and the solution is stirred overnight. After removal of solvent, the light colored oil is dissolved in toluene and is washed with hexanes. Drying under vacuum gives the product as a foam in 49% yield: $^1$H NMR (400 MHz, $C_6D_6$, δ): 1.43 (m, 2H), 3.06 (m, 2H), 3.52 (m, 2H), 4.07 (m, 2H), 6.22 (br s, 1H), 6.49 (m, 2H), 7.28 (m, 18H), 7.60 (m, 2H), 7.72 (m, 2H).

Example 4—Preparation of Zr Complex of 505-14 (505-17)

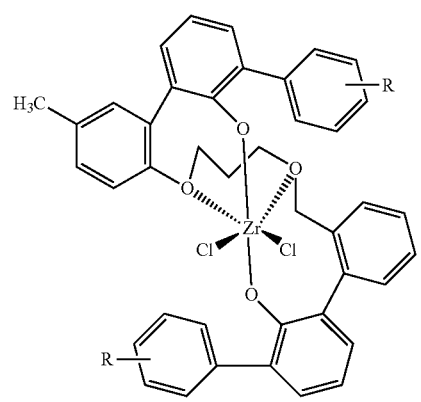

In the preceding structure, R=H. To the ligand 505-14 of Ex. 3 (540 mg) dissolved in 10 mL of toluene is added a 10 mL toluene solution of bis-benzyl-zirconium(IV) dichloride (ZrBn$_2$Cl$_2$) (380 mg). The reaction is stirred for 10 min at ambient temperature, and then heated at 85° C. for 1 h. The solution is concentrated to a quarter of its original volume and the formed solid is filtered away. The product is isolated by crystallization of the filtrate, giving 505-17 as a white solid: 1H NMR (400 MHz, CD$_2$Cl$_2$, δ): 1.57 (m, 1H), 2.10 (m, 1H), 2.42 (s, 3H), 3.42 (d, J=13.6 Hz, 1H), 3.78 (m, 3H), 4.60 (m, 1H), 4.82 (m, 1H), 6.82 (m, 1H), 6.91 (m, 2H), 7.01 (m, 2H), 7.38 (m, 17H), 7.74 (d, J=6.8 Hz, 2H).

Example 5—Preparation of 2-(3-((2'-hydroxy-2",5', 5"-trimethyl-[1,1':3',1"-terphenyl]-2-yl)methoxy) propoxy)-2",5,5',5"-tetramethyl-[1,1':3',1"-terphenyl]-2'-ol (505-23) (Ligand BP)

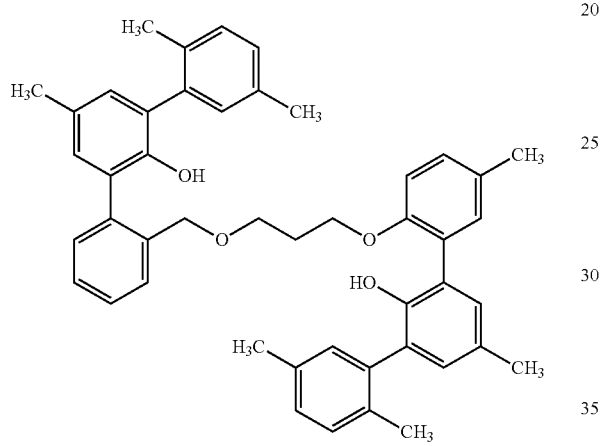

2-(3-((2'-hydroxy-2",5',5"-trimethyl-[1,1':3',1"-terphenyl]-2-yl)methoxy)propoxy)-2",5,5',5"-tetramethyl-[1,1':3', 1"-terphenyl]-2'-ol (505-23) is prepared using the procedure of Ex. 3 but using as starting materials 2',5,5'-trimethyl-2-((methoxymethoxy)-[1,1'-biphenyl]-3-yl lithium and 2-bromo-1-(3-((2-bromobenzyl)oxy)propoxy)-4-methylbenzene; $^1$H NMR (500 MHz, tol-d8, 363 K, δ): 1.67 (m, 2H), 2.16 (app m, 18H), 3.27 (m, 2H), 3.75 (m, 2H), 4.26 (s, 2H), 4.96 (s, 1H), 5.60 (s, 1H), 6.63 (d, J=8.5 Hz, 1H), 6.99 (m, 16H).

Example 6—Preparation of Zr Complex of 505-23

The procedure of Ex. 4 is repeated except that the product of Ex. 5 is employed in place of the product of Ex. 3.

The reaction scheme of the Examples 5 and 6 is as follows:

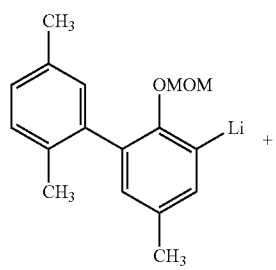

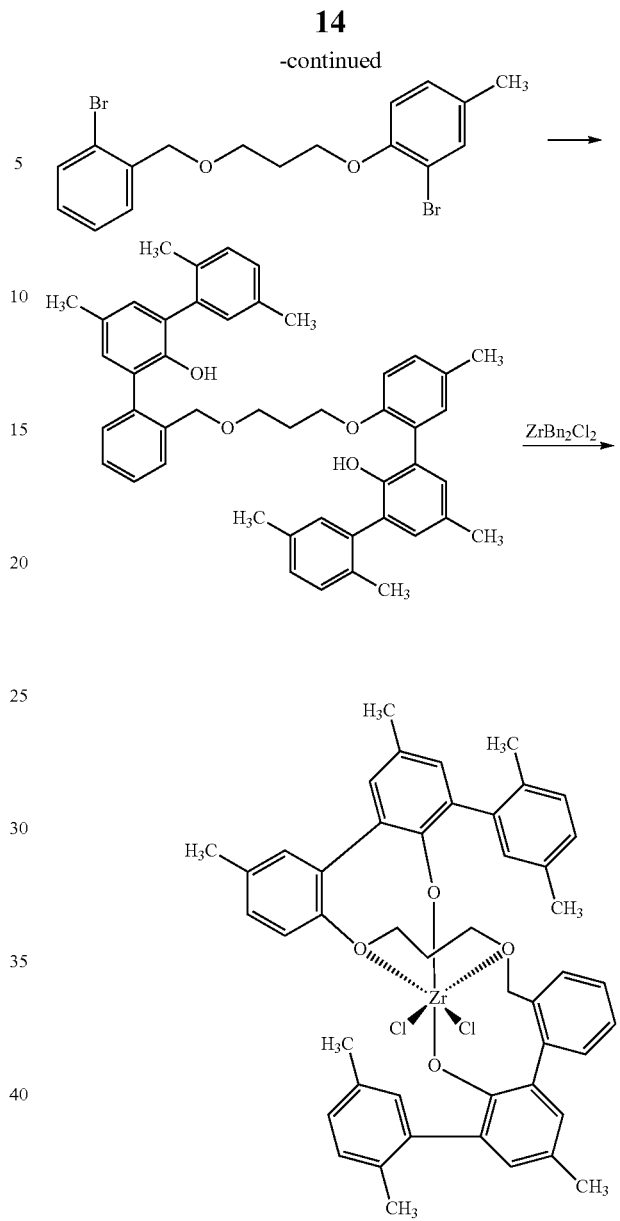

Example 7—Preparation of 2'-(3-((2'-hydroxy-5'-methyl-3'-(2-methylnaphthalen-1-yl)-[1,1'-biphenyl]-2-yl)methoxy)propoxy)-5,5'-dimethyl-3-(2-methylnaphthalen-1-yl)-[1,1'-biphenyl]-2-ol (509-42) (Ligand CP) and a Zirconium Complex Thereof

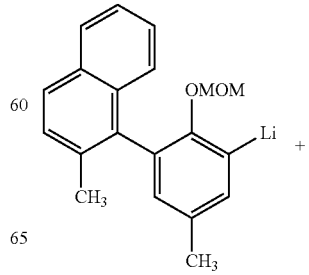

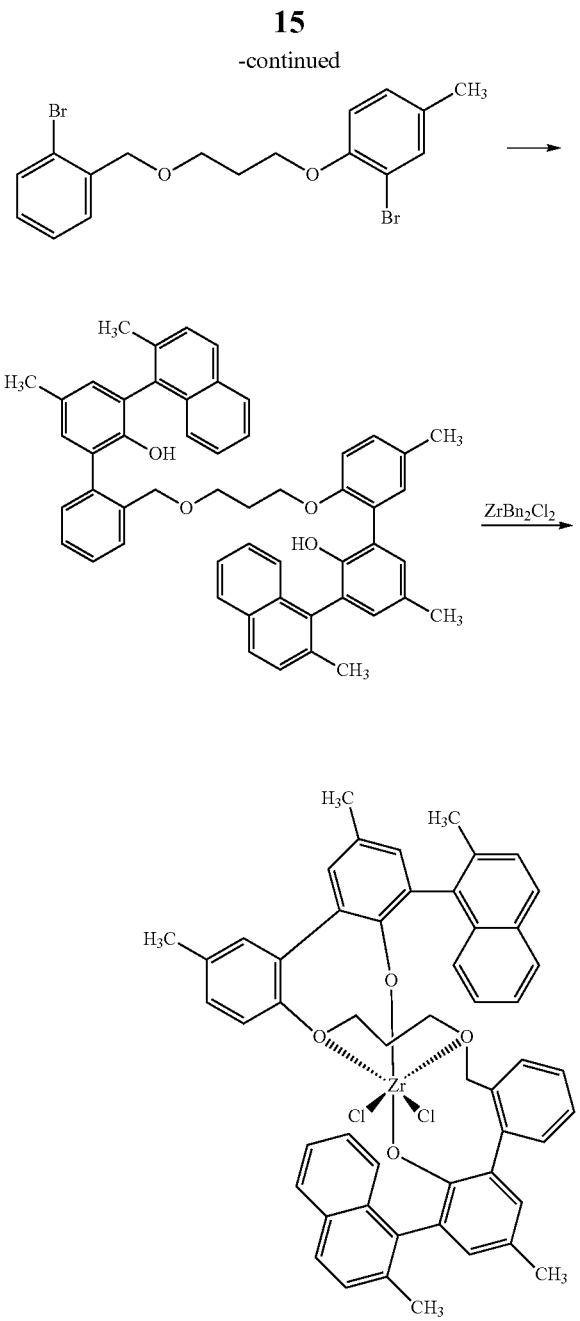

509-42 is prepared using the procedure of Ex. 3 but using as starting materials (2-(methoxymethoxy)-5-methyl-3-(2-methylnaphthalen-1-yl)phenyl) lithium (1.1 g, 3.0 mmol) and 2-bromo-1-(3-((2-bromobenzyl)oxy)propoxy)-4-methylbenzene; $^1$H NMR (500 MHz, tol-d8, 363 K, δ): 2.15 (s, 3H), 2.19 (s, 3H), 2.24 (s, 3H), 2.31 (d, J=8.5 Hz, 3H), 3.23 (m, 2H), 3.75 (m, 2H), 4.21 (m, 2H), 4.96 (br s, 1H), 5.60 (m, 1H), 6.57 (m, 1H), 6.85 (m, 3H), 6.98 (m, 2H), 7.15 (m, 11H), 7.68 (m, 7H); $^{13}$C NMR (125 MHz, CDCl$_3$, δ): 20.6, 20.57, 29.8, 30.2 (2 C), 66.9, 67.6, 74.9, 113 (2 C), 124.9-138.2 (39 C) 149.5, 150.3, 154.3.

To prepare the zirconium complex of 509-42, the procedure of Ex. 4 is repeated, except that the product of the preceding paragraph is employed in place of the product of Ex. 3 to form the zirconium complex shown in the preceding reaction scheme.

Example 8—Preparation of 2-((2-bromobenzyl)oxy)ethanol (509-13)

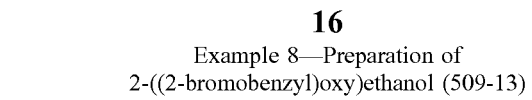

Sodium hydride (95%, 1.0 g, 40 mmol) is suspended in 20 mL of THF and is cooled to −35° C. Ethylene glycol (20 mL) is added slowly (Caution: H$_2$ generated) and the mixture is allowed to warm to ambient temperature over 10 min. 2-bromobenzylbromide (10 g, 40 mmol) is added and the reaction mixture is stirred overnight, then is quenched with saturated ammonium chloride. The product is extracted with 3 portions of ethyl acetate, followed by washes with water and brine. The organic portion is dried over MgSO$_4$, is filtered and is concentrated to a clear colorless oil in 84% crude yield: Rf=0.34 (30:70 acetone:isohexane); $^1$H NMR (500 MHz, CDCl$_3$, δ): 2.40 (br s, 1H), 3.66 (t, J=5.0 Hz, 2H), 3.78 (m, 2H), 4.62 (s, 2H), 7.15 (m, 1H), 7.31 (m, 1H), 7.47 (m, 1H), 7.53 (m, 1H); $^{13}$C NMR (125 MHz, CDCl$_3$, δ): 62.0, 72.1, 72.7, 123.2, 127.6, 129.39, 129.5, 132.8, 137.5; IR (cm$^{-1}$): 3406, 2924, 2866, 1440, 1353, 1205, 1109, 1069, 1026.

Example 9—Preparation of 2-bromo-1-(2-((2-bromobenzyl)oxy)ethoxy)-4-methylbenzene (509-20)

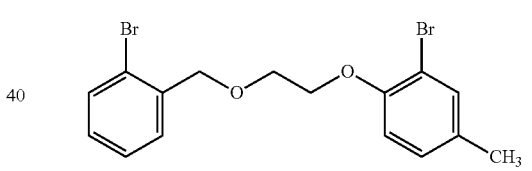

Alcohol 509-13 (3.8 g, 16.4 mmol) from Ex. 8, bromocresol (3.2 g, 17.2 mmol), and triphenylphosphine (4.5 g, 17.2 mmol) are dissolved in 20 mL of THF. DIAD (3.4 mL, 17.5 mmol) is added dropwise as the colorless solution slowly turns yellow. The reaction mixture is stirred at ambient temperature overnight then quenched with saturated ammonium chloride. The mixture is extracted with ethyl acetate and is concentrated to a crude yellow oil. Pentane is slurried with the oil and the slurry is filtered through a plug of silica gel. The filtrate is concentrated giving the product as a solid that is recrystallized in acetone/pentane in 45% yield: $^1$H NMR (400 MHz, CDCl$_3$, δ): 2.28 (s, 3H), 3.97 (t, J=5.0 Hz, 2H), 4.23 (t, J=4.75 Hz, 2H), 4.76 (s, 2H), 6.83 (m, 1H), 7.04 (m, 1H), 7.15 (m, 1H), 7.33 (m, 1H), 7.38 (s, 1H), 7.55 (m, 1H); $^{13}$C NMR (125 MHz, CDCl$_3$, δ): 20.4, 69.3, 72.9, 112.3, 113.9, 122.8, 127.6, 129.0, 129.1, 129.3, 132.1, 132.7, 134.0, 137.8, 153.4; IR (cm$^{-1}$): 2921, 2865, 1492, 1438, 1278, 1250, 1103, 1022, 798.

An overview of the reaction scheme of Examples 8 and 9 is as follows:

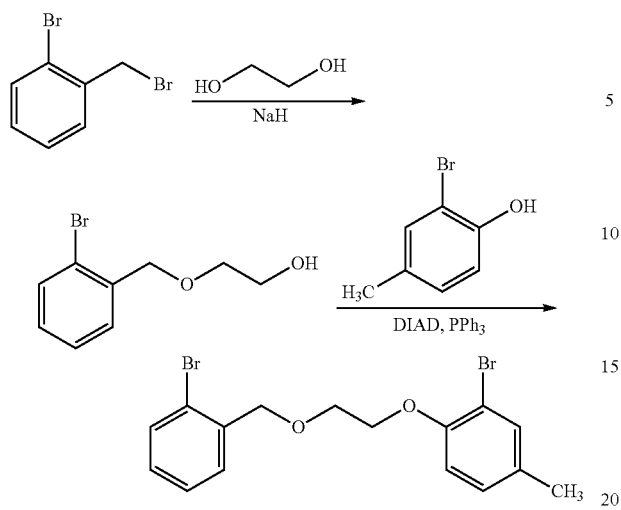

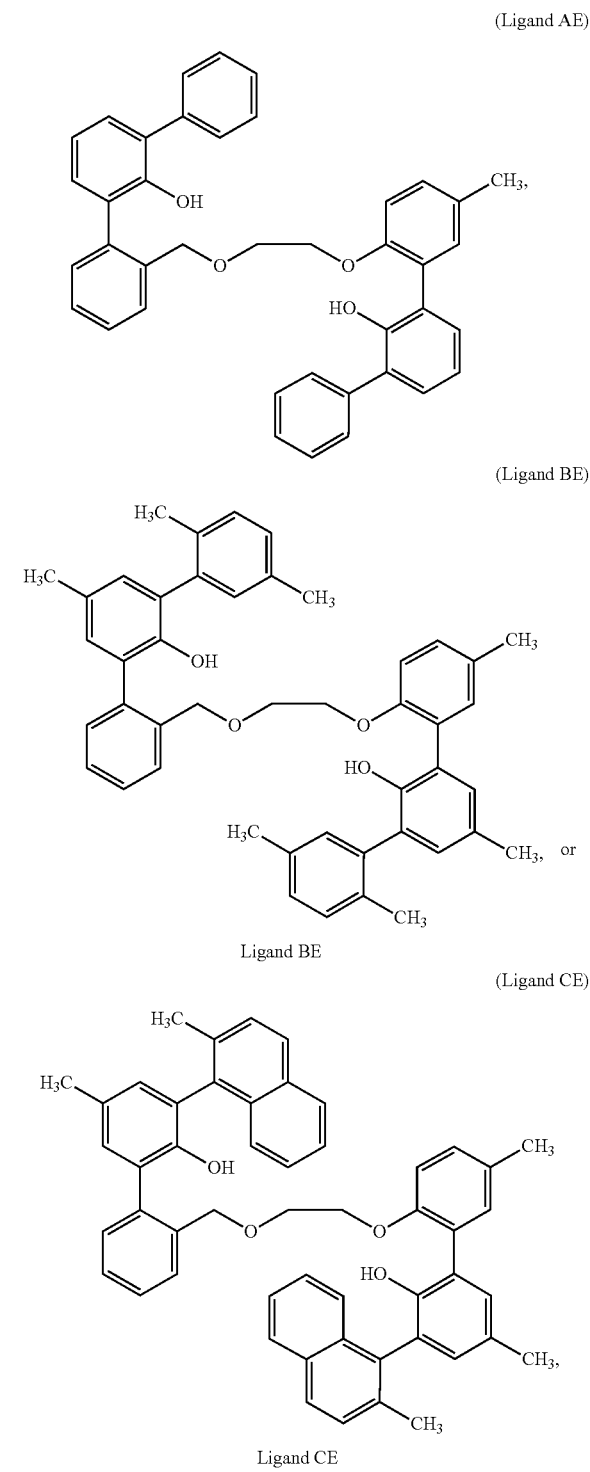

What is claimed is:

1. A process for preparing a ligand, the process comprising contacting 3-((2-bromobenzyl)oxy)propan-1-ol with bromocresol and triphenylphosphine in a reaction medium under reaction conditions, thereby forming a 2-bromo-1-(3-((2-bromobenzyl)oxy)propoxy)-4-methylbenzene;

contacting a first reactant with a bridging reactant in a polar aprotic reaction medium under reaction conditions, thereby forming the ligand; wherein: (a) when the first reactant is 2-((tetrahydro-2H-pyran-2-yl)oxy)-[1,1'-biphenyl]-3-yl lithium, the bridging reactant is 2-bromo-1-(3-((2-bromobenzyl)oxy)propoxy)-4-methylbenzene, and the ligand is 2-(3-((2'-hydroxy-[1,1':3',1''-terphenyl]-2-yl)methoxy)propoxy)-5-methyl-[1,1':3',1''-terphenyl]-2'-ol (Ligand AP); or wherein (b) when the first reactant is 2',5,5'-trimethyl-2-((methoxymethoxy)-[1,1'-biphenyl]-3-yl lithium, the bridging reactant is 2-bromo-1-(3-((2-bromobenzyl)oxy)propoxy)-4-methylbenzene, and the ligand is 2-(3-((2'-hydroxy-2'',5',5''-trimethyl-[1,1':3',1''-terphenyl]-2-yl)methoxy)propoxy)-2'',5,5',5''-tetramethyl-[1,1':3',1''-terphenyl]-2'-ol (Ligand BP); or wherein (c) when the first reactant is 2-(methoxymethoxy)-5-methyl-3-(2-methylnaphthalen-1-yl)phenyl) lithium, the bridging reactant is 2-bromo-1-(3-((2-bromobenzyl)oxy)propoxy)-4-methylbenzene, and the ligand is 2'-(3-((2'-hydroxy-5'-methyl-3'-(2-methylnaphthalen-1-yl)-[1,1'-biphenyl]-2-yl)methoxy)propoxy)-5,5'-dimethyl-3-(2-methylnaphthalen-1-yl)-[1,1'-biphenyl]-2-ol (Ligand CP).

2. The process of claim 1 further comprising a second preliminary step to prepare the 3-((2-bromobenzyl)oxy)propan-1-ol, the second preliminary step comprising contacting 1,3-propanediol with 2-bromobenzylbromide in a reaction medium under reaction conditions, thereby forming the 3-((2-bromobenzyl)oxy)propan-1-ol.

3. The process of claim 1 wherein the bridging reactant is a 2-bromo-1-(2-((2-bromobenzyl)oxy)ethoxy)-4-methylbenzene, and the ligand is Ligand AE respectively.

4. The process of claim 3 wherein the 2-bromo-1-(2-((2-bromobenzyl)oxy)ethoxy)-4-methylbenzene is prepared by a process comprising contacting 2-((2-bromobenzyl)oxy)ethanol with bromocresol in a reaction medium under reaction conditions, thereby forming the 2-bromo-1-(2-((2-bromobenzyl)oxy)ethoxy)-4-methylbenzene.

5. The process of claim 4 wherein the 2-((2-bromobenzyl)oxy)ethanol is prepared by a process comprising contacting ethylene glycol with 2-bromobenzylbromide in a reaction medium under reaction conditions, thereby forming the 2-((2-bromobenzyl)oxy)ethanol.

6. The process of claim 1 further comprising contacting the ligand with bis-benzyl-zirconium(IV) dichloride ($ZrBn_2Cl_2$) in a reaction medium under reaction conditions, thereby forming the zirconium complex of the ligand.

* * * * *